(12) United States Patent
Hiro et al.

(10) Patent No.: US 6,852,226 B2
(45) Date of Patent: Feb. 8, 2005

(54) WASTE TREATMENT SYSTEM FOR TREATMENT OF ORGANIC WASTE AND DIGESTED LIQUID THEREOF

(75) Inventors: Naoki Hiro, Osaka (JP); Masaki Moriizumi, Moriyama (JP); Jun Hirose, Hirakata (JP); Naoki Kitayama, Moriyama (JP); Fumitake Kondo, Otsu (JP)

(73) Assignee: Sanyo Electric Co., Ltd., Osaka (JP)

( * ) Notice: Subject to any disclaimer, the term of this patent is extended or adjusted under 35 U.S.C. 154(b) by 0 days.

(21) Appl. No.: 10/656,112

(22) Filed: Sep. 8, 2003

(65) Prior Publication Data

US 2004/0045885 A1 Mar. 11, 2004

(30) Foreign Application Priority Data

Sep. 10, 2002 (JP) ....................................... 2002-263649
Aug. 1, 2003 (JP) ....................................... 2003-205367

(51) Int. Cl.[7] .............................. C02F 3/28; C02F 1/461
(52) U.S. Cl. ....................... 210/603; 210/631; 210/748; 210/198.1; 210/259
(58) Field of Search ................................ 210/603, 906, 210/631, 748, 252, 259, 198.1; 71/10

(56) References Cited

U.S. PATENT DOCUMENTS 3,336,220 A * 8/1967 Neidl .......................... 210/603
3,711,392 A * 1/1973 Metzger ...................... 210/603
3,914,164 A * 10/1975 Clark .......................... 210/602
4,090,940 A * 5/1978 Switzgable .................. 204/278
5,702,572 A * 12/1997 Fujimura et al. ......... 204/157.15
6,299,774 B1 * 10/2001 Ainsworth et al. ......... 210/603

FOREIGN PATENT DOCUMENTS

| JP | 2002-151131 | | 5/2002 |
| JP | P2003-181456 A | * | 7/2003 |
| JP | P2004-130186 A | * | 4/2004 |

* cited by examiner

Primary Examiner—Fred G. Prince
(74) Attorney, Agent, or Firm—Westerman, Hattori, Daniels & Adrian, LLP (57) ABSTRACT

A waste treatment system permitting treatment of organic wastes at low cost is provided. In the waste treatment system, organic wastes such as sewage, garbage and sludge are introduced into a methane fermentation bath for anaerobic fermentation. The methane gas produced in the bath is refined in a gas holder and then supplied to an electric generator, where the methane gas is used as a raw material for power generation. Digested liquid within the methane fermentation bath is supplied to an electrolytic bath via a flow adjustment bath and a fine screen. In the electrolytic bath, the digested liquid is subjected to electrolysis, by applying potentials to an electrode pair in the electrolytic bath based on the electric power obtained by the electric generator. By the electrolysis, nitrogen components including organic nitrogen and ammonia nitrogen, and BOD, SS and phosphorus components are removed from the digested liquid.

11 Claims, 5 Drawing Sheets

WASTE TREATMENT SYSTEM FOR TREATMENT OF ORGANIC WASTE AND DIGESTED LIQUID THEREOF

BACKGROUND OF THE INVENTION

1. Field of the Invention

The present invention relates to a waste treatment system, and more particularly to a waste treatment system for treatment of organic waste and digested liquid of the organic waste.

2. Description of the Background Art

A technique for treating organic waste and recovering electric energy and thermal energy during the treatment has conventionally been disclosed (e.g., in Japanese Patent Laying-Open No. 2002-151131). With this technique, organic waste is subjected to anaerobic fermentation to obtain methane gas. The digested sludge is then dewatered and converted into a low molecular weight substance to also obtain methane gas. The methane gas thus obtained is used as fuel for a fuel cell.

The digested liquid from the anaerobic fermentation described above, however, requires removal of nitrogen upon effluent disposal. If the removal of nitrogen is to be conducted by microbial treatment, a large amount of methanol is necessary as hydrogen donor, and a polymer flocculant and a large-scale processing bath are also required, leading to an increased cost. The organic waste treatment also needs removal of phosphorus, which requires an additional cost of introducing a chemical agent or the like, and also requires complicated processing for adjusting pH.

SUMMARY OF THE INVENTION

The present invention has been conceived in view of the foregoing, and its object is to provide a waste treatment system allowing treatment of organic waste at low cost.

A waste treatment system according to the present invention includes an electric generating device generating electric power using a valuable substance recovered from organic waste as fuel, a methane fermentation bath anaerobically fermenting the organic waste, and an electrolytic bath into which digested liquid generated upon fermentation in the methane fermentation bath is introduced. The electrolytic bath has an electrode pair fed with the electric power from the electric generating device.

According to the present invention, it is possible to remove ammonia, organic nitrogen and nitrogen oxide within the digested liquid as nitrogen gas in the electrolytic bath by oxidation-reduction. Further, in the electrolytic bath, the vicinity of the cathode electrode can be made alkaline (pH 10–14) by the electrolysis. Thus, it is possible to remove the phosphorus components within the digested liquid by crystallizing the same as phosphate. As such, in the waste treatment system, methanol for microbial treatment and a large-scale processing bath become unnecessary for removal of nitrogen in the digested liquid after fermentation of the organic waste. Further, the phosphorus components can be combined with calcium ions, magnesium ions, or iron ions within the digested liquid in an electrochemical manner, to obtain solid-state compounds separable from the digested liquid. Thus, it is possible to remove the phosphorus components from the digested liquid without using a chemical agent or the like.

Further, according to the present invention, the electric power recovered from the waste can be utilized within the same system. Thus, the electric power obtained can be used efficiently, with power loss during transmission or the like being restricted to the least possible level.

Still further, according to the present invention, increase/decrease in amount of the electric power that can be fed from the electric generating device to the electrode pair of the electrolytic bath corresponds to increase/decrease in amount of the electric power that should be fed to the electrode pair of the electrolytic bath, for the following reasons. The increase/decrease in amount of the electric power that can be fed from the electric generating device to the electrode pair of the electrolytic bath corresponds to increase/decrease in amount of methane gas that is introduced into the electric generating device. The increase/decrease in amount of the methane gas introduced into the electric generating device in turn corresponds to increase/decrease in amount of the digested liquid that is introduced into the electrolytic bath. The increase/decrease in amount of the digested liquid introduced into the electrolytic bath then corresponds to the increase/decrease in amount of the electric power that should be fed to the electrode pair of the electrolytic bath. As such, the waste treatment system becomes a stable system wherein even if there occurs an increase or a decrease in amount of the digested liquid to be processed in the electrolytic bath, the increase/decrease in amount of the electric power that needs to be fed from another device other than the electric generating device to the electrode pair of the electrolytic bath can be restricted to the least possible level, and wherein even if there occurs an increase or a decrease in amount of the methane gas obtained by fermentation of the waste, the increase/decrease in amount of excessive power, i.e., the electric power other than that fed to the electrode pair of the electrolytic bath, can be restricted to the least possible level.

Preferably, the waste treatment system according to the present invention further includes a bubble separating portion separating bubbles from the liquid in the electrolytic bath.

With this configuration, the solid matters such as the phosphorus components and others can be separated from the digested liquid by the bubbles generated during the electrolysis in the electrolytic bath, without using a chemical agent such as a flocculant. SS (suspended solids) components included in the digested liquid can also be removed.

Preferably, in the waste treatment system according the present invention, the electrode pair includes an anode electrode formed of platinum or a conductor containing platinum, and a cathode electrode formed of a copper-zinc alloy, a conductor containing iron, or a conductor containing aluminum.

This improves the capability of removing the nitrogen components from the digested liquid in the electrolytic bath.

Still preferably, the waste treatment system according to the present invention further includes a surfactant adding portion adding a surfactant to the digested liquid introduced into the electrolytic bath.

With this configuration, the bubbles generated in the electrolytic bath can be made smaller in size, so that the rise of the liquid level due to the bubbling within the electrolytic bath can be suppressed.

Still preferably, the waste treatment system according to the present invention further includes a chemical agent adding portion adding chloride or hypochlorite to the digested liquid introduced into the electrolytic bath.

This improves the nitrogen removing capability by electrolysis in the electrolytic bath. Particularly when calcium chloride is added, the phosphorus component combines with the calcium ion, so that the phosphorus removing capability in the electrolytic bath is also improved.

Still preferably, the waste treatment system according to the present invention further includes a polarity control portion inverting polarities of potentials applied from the electric generating device to the electrode pair.

With this configuration, the both electrodes constituting the electrode pair can be made to serve as the anode electrode where oxygen is generated during the electrolytic process of water. Thus, it is possible to cause gas to be generated on the respective electrode of the electrode pair. It is also possible to change the polarity of the electrode on which phosphate has been deposited by the above-described reaction, to acidify the liquid in the vicinity of the relevant electrode. Accordingly, the scales deposited on the both electrodes can be removed by the electrolytic reaction.

Still preferably, the waste treatment system according to the present invention further includes a solid matter separating portion separating a solid matter from the digested liquid before the digested liquid is introduced into the electrolytic bath.

With this configuration, the situation where solid matters are deposited on the electrodes in the electrolytic bath and interfere with the electrolytic reaction can be avoided reliably.

Still preferably, in the waste treatment system according to the present invention, the solid matter separating portion is formed of a film separating the solid matter having a particle size equal to or greater than a prescribed size from the digested liquid.

Still preferably, in the waste treatment system according to the present invention, the electric generating device outputs direct current (DC) power.

With this configuration, when a fuel cell, for example, is used as the electric generating device in the waste treatment system, the fuel cell outputs the DC power. Thus, it is unnecessary to provide a device for converting electric power output from the electric generating device to the DC power to supply to the electrode pair. This can reduce the space occupied by the system.

Still preferably, in the waste treatment system according to the present invention, the electric generating device outputs DC power of a constant current or a constant voltage.

With this configuration, it is possible to feed stable power to the electrode pair in the electrolytic bath in the waste treatment system. Accordingly, the water treatment capacity of the electrolysis in the electrolytic bath becomes stable.

Still preferably, in the waste treatment system according to the present invention, the electric generating device and the electrolytic bath are configured integrally.

This permits the electric generating device and the electrolytic bath to be accommodated in one and the same casing, for example, so that the space occupied by the system can further be reduced.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Hereinafter, embodiments of the present invention are described with reference to the drawings. In the following description, the same portions are denoted by the same reference characters and their names and functions are also the same, unless otherwise stated. Thus, detailed description thereof is not repeated.

Figure 1:
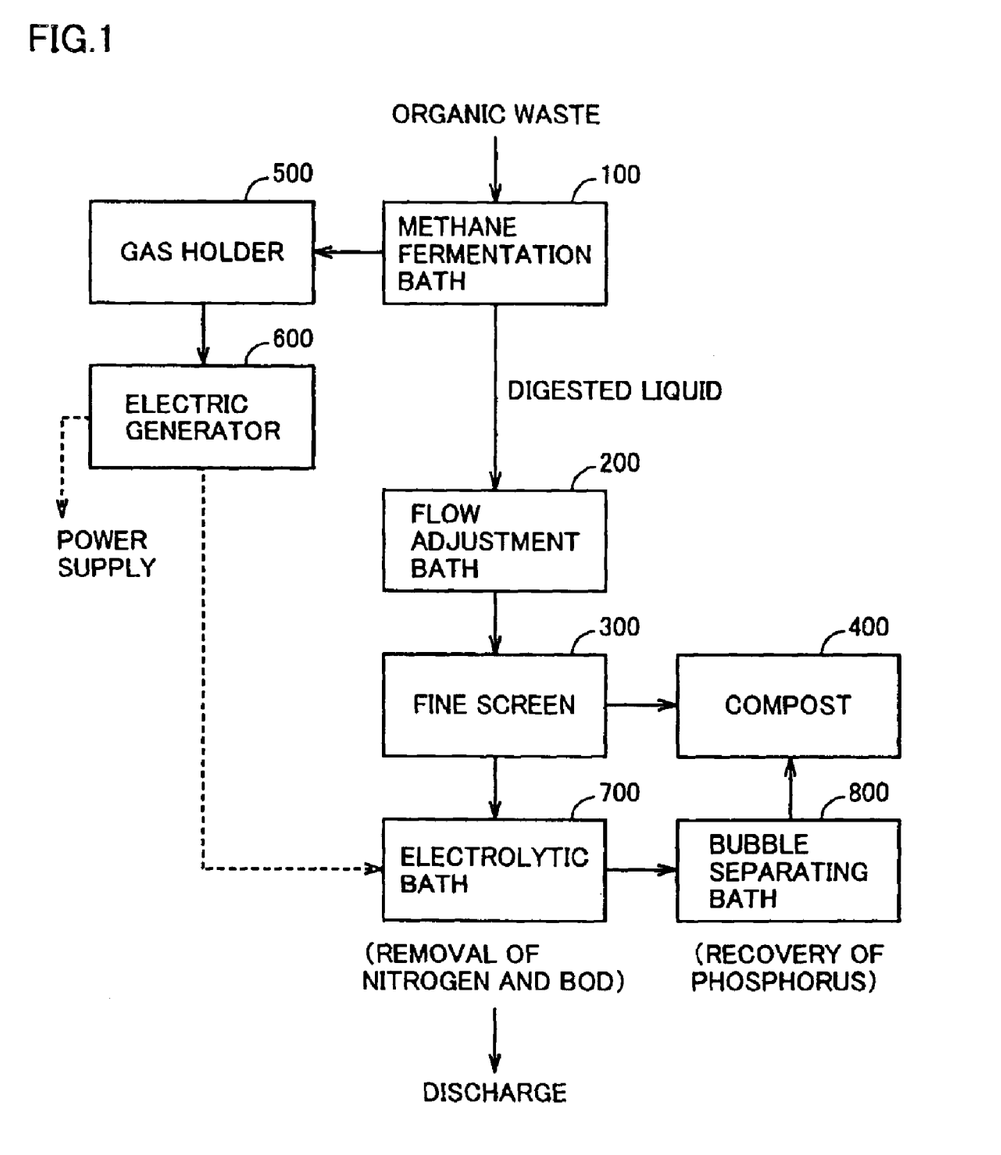
FIG. 1 shows a process flow in a waste treatment system according to an embodiment of the present invention.

FIG. 1 shows a process flow in the waste treatment system according to an embodiment of the present invention.

In the waste treatment system, organic wastes, such as night soil, raw garbage, sludge and others, are introduced into a methane fermentation bath 100 for anaerobic fermentation. Methane fermentation bath 100 is maintained at a condition where the conversion ratio of the introduced wastes into gases becomes highest, i.e., at 35–55° C. and with pH of 6–8, for example. Methane fermentation bath 100 is provided with means for agitating the contents therein.

In methane fermentation bath 100, fermentation is conducted for a prescribed time period. The methane gas produced is refined in a gas holder 500, and then supplied to an electric generator 600. The methane gas is used as a raw material for generation of electric power in electric generator 600. Some of the electric power obtained at electric generator 600 is used for electrolysis at an electrolytic bath 700, as will be described later, and the remaining power is fed to other devices.

Digested liquid within methane fermentation bath 100 is provided to a flow adjustment bath 200. The digested liquid within flow adjustment bath 200 is passed through a fine screen 300 in prescribed amounts to remove solid matters therefrom, and then provided to electrolytic bath 700. Fine screen 300 is a film for removal of solid matters having a particle size of greater than some hundred $\mu$m. The solid matters captured by fine screen 300 are delivered to a compost 400.

In electrolytic bath 700, the digested liquid is subjected to electrolysis. The electrolysis in electrolytic bath 700 is performed by applying potentials to an electrode pair in electrolytic bath 700 based on the electric power obtained at electric generator 600. By the electrolysis, nitrogen components including organic nitrogen and ammonia nitrogen are removed from the digested liquid, as will be described later. Further, a bubble separating bath 800 is connected to electrolytic bath 700. In electrolytic bath 700, gas is produced by electrolyzation of water. Such generation of gas makes phosphorus compounds, BOD (biochemical oxygen demand) components and SS components within the digested liquid rise to the liquid level together. Bubble separating bath 800 functions to separate the bubbles containing the phosphorus compounds from the digested liquid.

The bubbles separated in bubble separating bath 800 are delivered to compost 400.

The digested liquid in electrolytic bath 700, having the nitrogen, phosphorus and BOD components thus removed therefrom, is then discharged from electrolytic bath 700 to the outside.

Figure 2:
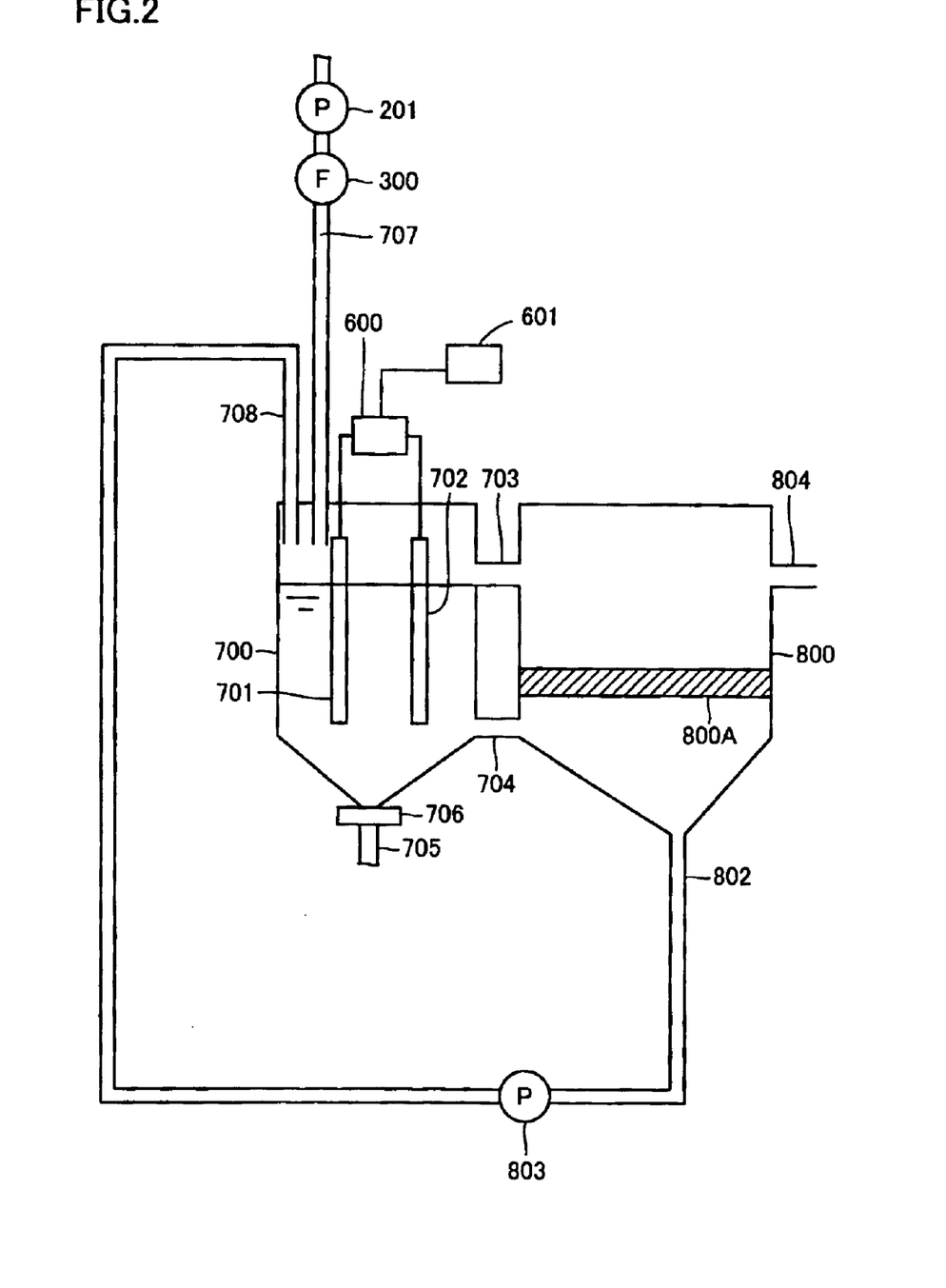
FIG. 2 schematically shows structures of the electrolytic bath and the bubble separating bath shown in FIG. 1.

FIG. 2 schematically shows structures of electrolytic bath 700 and bubble separating bath 800.

Electrolytic bath 700 is provided with an electrode pair of electrodes 701, 702. Electric power generated by electric generator 600 is fed to the pair of electrodes 701, 702. Feeding of the electric power from electric generator 600 to electrodes 701, 702 is controlled by a power control portion 601, and the liquid in electrolytic bath 700 is discharged via an outlet 705 after completion of the electrolysis. Power control portion 601 makes one and the other of electrodes 701, 702 an anode electrode and a cathode electrode, respectively.

The digested liquid is introduced into electrolytic bath 700 in specific amounts at regular intervals, from a tube 707 via a pump 201 provided at flow adjustment bath 200 and fine screen 300 formed of a filter.

Outlets 703, 704 are formed on a side of electrolytic bath 700. Outlet 705 formed at the bottom of electrolytic bath 700 is opened/closed by a valve 706, which is controlled by a control circuit (not shown).

Outlets 703, 704 are provided at upper and lower portions, respectively, of electrolytic bath 700, and are connected to bubble separating bath 800. Bubbles generated in electrolytic bath 700, as will be described later, are delivered via outlet 703 to bubble separating bath 800. The liquid within electrolytic bath 700 is delivered via outlet 704 to bubble separating bath 800.

Bubble separating bath 800 is provided with a filter 800A at an intermediate level in height. Filter 800A separates the bubbles from the liquid supplied from electrolytic bath 700. The bubble-containing portion is delivered to compost 400 via an outlet 804 provided at a position upper than filter 800A. The liquid portion is discharged from an outlet 802 provided lower than filter 800A at the bottom of bubble separating bath 800.

Outlet 802 is connected to a pump 803. The liquid from which the bubbles have been removed in bubble separating bath 800 is delivered back to electrolytic bath 700 by pump 803, via outlet 802 and tube 708.

The digested liquid supplied from methane fermentation bath 100 via flow adjustment bath 200 and fine screen 300 to electrolytic bath 700 is circulated by pump 803 through electrolytic bath 700 and bubble separating bath 800 for a prescribed time period, during which the digested liquid undergoes the electrolytic process using electrodes 701, 702. The bubbles generated are separated and delivered from bubble separating bath 800 to compost 400.

Reactions during the electrolysis in electrolytic bath 700 are now described.

On the cathode electrode side, as expressed by the following chemical equations (1)–(5), hydrogen gas and hydroxide ions are produced. At the same time, by virtue of their vigorous catalytic activities, organic nitrogen is reduced to ammonia via nitric acid and nitrous acid ions.

$$H_2O + e^- \Leftrightarrow \tfrac{1}{2}H_2\uparrow + OH^- \tag{1}$$

$$NO_3^- + H_2O + 2e^- \Leftrightarrow NO_2^- + 2OH^- \tag{2}$$

$$NO_2^- + 5H_2O + 6e^- \Leftrightarrow NH_3 + 7OH^- \tag{3}$$

$$NO_2^- + 7H^+ + 6e^- \Leftrightarrow NH_3 + 2H_2O \tag{4}$$

$$NO_2^- + 8H^+ + 6e^- \Leftrightarrow NH_4 + 2H_2O \tag{5}$$

On the anode electrode side, as expressed by the following chemical equations (6)–(8), chlorine is generated at the same time as generation of oxygen, and the chlorine is further oxidized to hypochlorous acid.

$$H_2O \Leftrightarrow \tfrac{1}{2}O_2\uparrow + 2H^+ + 2e^- \tag{6}$$

$$2Cl^- \Leftrightarrow Cl_2\uparrow + 2e^- \tag{7}$$

$$Cl_2 + H_2O \Leftrightarrow H^+ + Cl^- + HClO \tag{8}$$

Ammonia generated on the cathode electrode side is oxidized by liquid phase reaction with the hypochlorous acid or the like to produce nitrogen gas, as shown by the following equation (9). This reaction is promoted by adding chloride or hypochlorite to electrolytic bath 700. In this regard, the system of the present embodiment preferably includes a device for adding chloride or hypochlorite (especially, calcium chloride) to electrolytic bath 700.

$$\tfrac{2}{3}NH_3 + HClO \rightarrow \tfrac{1}{3}N_2\uparrow + HCl + H_2O \tag{9}$$

Calcium ions in the digested liquid are attracted toward the cathode electrode by the electrolysis. In the vicinity of the cathode electrode, the alkali concentration increases (to pH 10–14) by the reaction of equation (1) above. Thus, in the vicinity of the cathode electrode, phosphoric acid ions within the digested liquid are crystallized as hydroxyapatite, as expressed by the following equation (10), which is deposited on the cathode electrode.

$$10Ca^{2+} + 2OH^- + 6PO_4^{3-} \rightarrow Ca_{10}(OH)_2(PO_4)_6 \tag{10}$$

(hydroxyapatite)

Power control portion 601 switches the polarities applied to electrodes 701, 702 when the deposition of the crystals on the cathode electrode reaches a prescribed level. Thus, of electrodes 701 and 702, the one having served as the cathode electrode on which the crystals have deposited is made now to serve as the anode electrode. On the anode electrode, as shown by equation (6) above, hydrogen gas is generated as the vicinity of the electrode is acidified, so that the deposited crystals are separated from the electrode and rise to the liquid level with the bubbles. The crystals thus floating are delivered to bubble separating bath 800 as described above.

As such, the nitrogen and phosphorus compounds are removed from the digested liquid by the electrolysis in electrolytic bath 700.

In the case where one of electrodes 701, 702 is formed of a conductor containing iron, iron is dissolved when the relevant electrode is made to serve as a cathode electrode, and ferric phosphate is generated as expressed by the following equation (11). This improves the phosphorus removing capability of electrolytic bath 700. As such, it is preferable to form one of electrodes 701, 702 with a conductor containing iron.

$$Fe^{3+} + PO_4^{3-} \rightarrow FePO_4 \tag{11}$$

Further, it is preferable that the anode electrode is formed of platinum or a conductor containing platinum to ensure efficient reactions on the anode electrode side as shown by equations (6)–(8) above.

Still further, it is preferable to provide a device for introducing a surfactant into electrolytic bath 700. This can reduce the size of the bubbles generated within electrolytic bath 700, thereby suppressing the rise of the liquid level due to the bubbling in electrolytic bath 700. The surfactant may be mixed to the digested liquid before the digested liquid is introduced into electrolytic bath 700, if possible.

Specific effects of the removal of the nitrogen compounds and the phosphorus compounds in the present embodiment are shown in Table 1.

TABLE 1

| Raw Water (after separation) | SS (mg/L) | T-P (mg/L) | T-N (mg/L) |
| --- | --- | --- | --- |
| Before Electrolysis | 6,660 | 300 | 2,300 |
| After Electrolysis | — | 5 | 50 |

Current condition: 7A/L
Anode electrode: platinum-iridium
Cathode electrode: brass Table 1 shows SS component concentrations, total phosphorus concentrations (T-P) and total nitrogen concentrations (T-N) in the digested liquid before and after the processing in electrolytic bath 700. The results shown in Table 1 were obtained as follows. In electrolytic bath 700, a current of 7 A/L (ampere/little) was applied to electrodes 701, 702 for four hours. The polarities of electrodes 701, 702 were switched with each other every four hours. Platinum-iridium was used for electrode 701, and brass was used for electrode 702.

As seen from Table 1, the SS components can be removed completely by using electrolytic bath 700 of the present embodiment. Further, the nitrogen and phosphorus concentrations are both reduced by about 98%.

Figure 3:
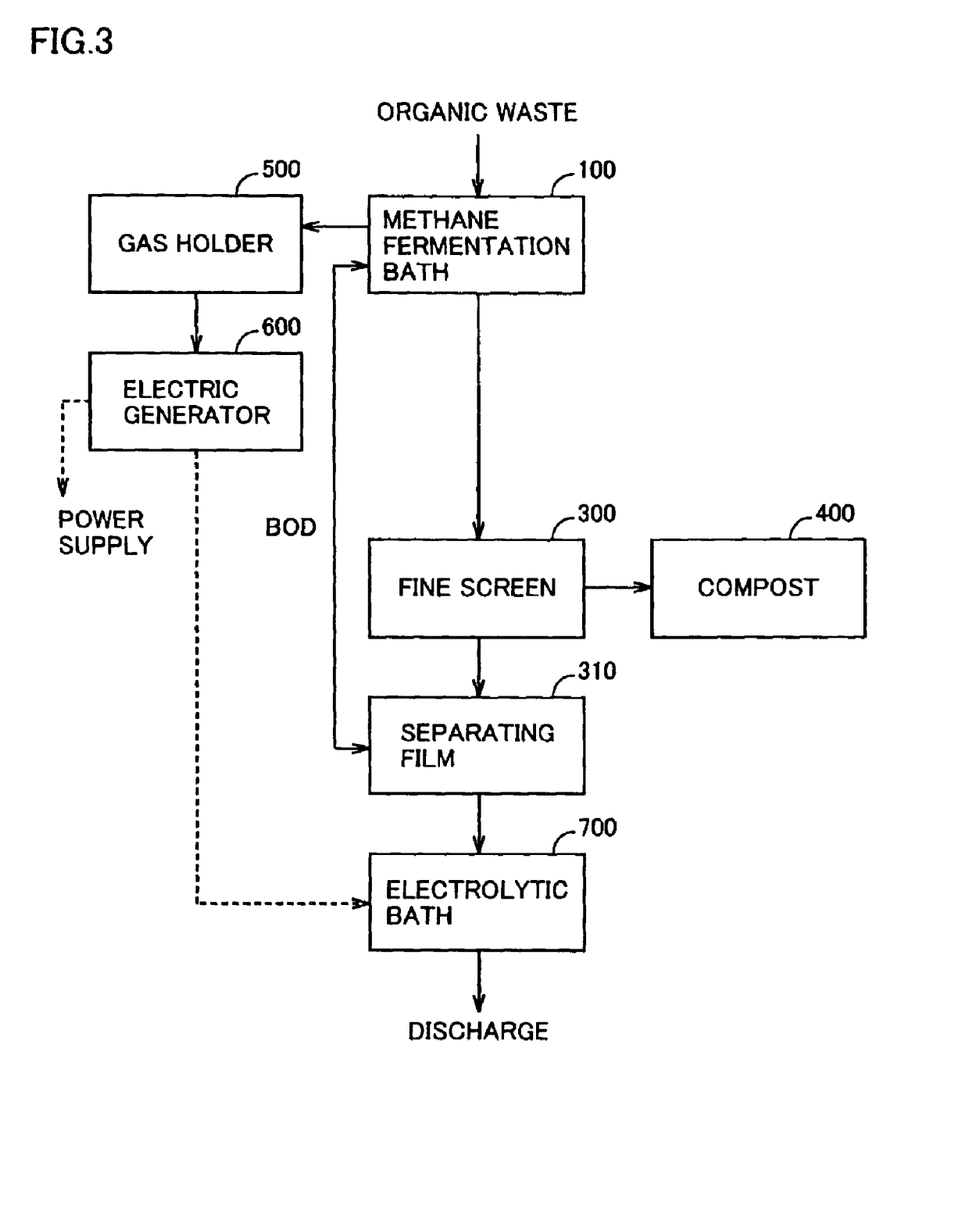
FIG. 3 shows a process flow in a modification of the waste treatment system of FIG. 1.

FIG. 3 shows a process flow in a modification of the waste treatment system of FIG. 1.

In the waste treatment system shown in FIG. 3, organic wastes are introduced into methane fermentation bath 100. The methane gas generated in methane fermentation bath 100 is refined in gas holder 500, and then supplied to electric generator 600.

The digested liquid within methane fermentation bath 100 is passed through fine screen 300 before being provided to a separating film 310. Separating film 310 is a film for removing solid matters having a particle size of more than some hundred μm.

The digested liquid passed through separating film 310 is subjected to electrolysis in electrolytic bath 700 before discharge.

Figure 4:
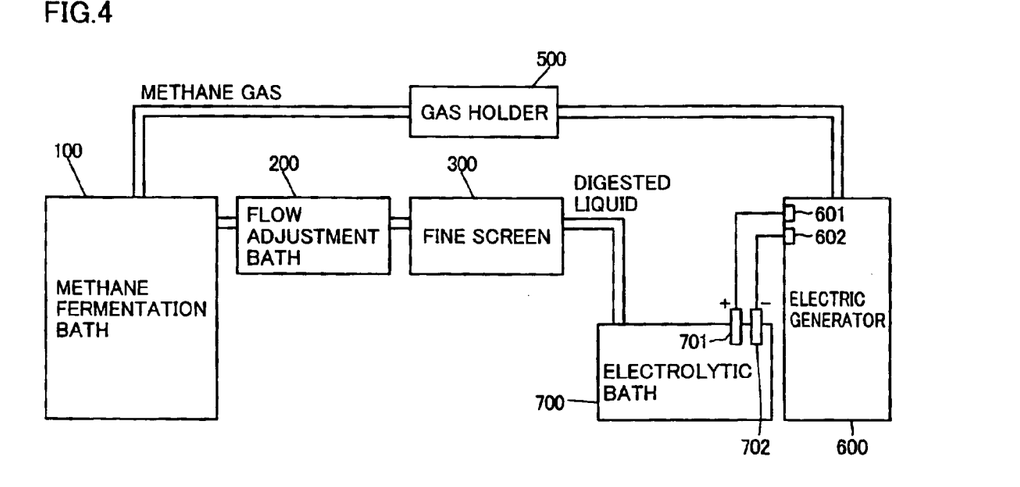
FIG. 4 is a structural diagram illustrating a modification of the waste treatment system of FIG. 1 where the electrolytic bath and the electric generator are constructed integrally.

In the waste treatment system described above, it is preferable that electric generator 600 is configured to supply DC power, that electrolytic bath 700 and electric generator 600 are formed integrally, and that electrodes 701, 702 of electrolytic bath 700 are directly connected to electric generator 600. The structures of electrolytic bath 700 and electric generator 600 in such a modification of the waste treatment system of FIG. 1 are shown in FIG. 4. Compost 400 and bubble separating bath 800 shown in FIG. 1 are not shown in FIG. 4.

Referring to FIG. 4, in the waste treatment system, the digested liquid is delivered from methane fermentation bath 100 to electrolytic bath 700 via flow adjustment bath 200 and fine screen 300. The methane gas is delivered from methane fermentation bath 100 to electric generator 600 via gas holder 500.

Electric generator 600 of the present embodiment is equipped with a device for converting alternate current (AC) power generated to DC power for feeding. Further, electric generator 600 is equipped with a stabilizer device for stabilizing voltage and/or current of the electric power being fed to a constant level. That is, the electric power generated by electric generator 600 is converted to the DC power and stabilized by the stabilizer device before being fed to output terminals 601, 602.

Power generator 600 has output terminals 601, 602 for outputting the DC power. Electrodes 701, 702 within electrolytic bath 700 are directly connected to output terminals 601, 602, respectively. As such, electric generator 600 and electrolytic bath 700 are configured integrally in the present embodiment, and therefore, they may be accommodated in one and the same casing.

Figure 5:
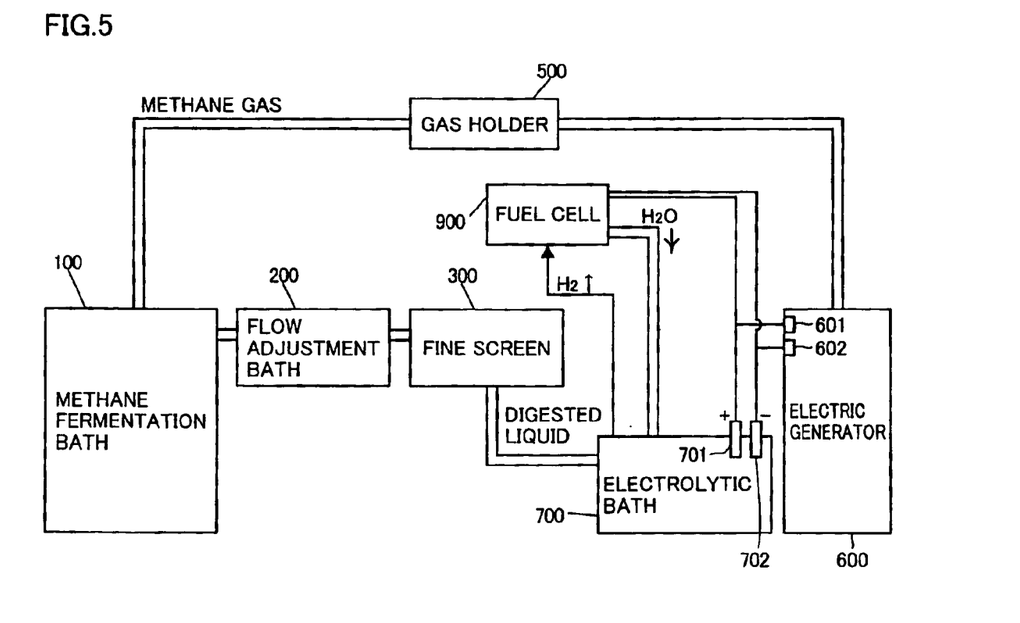
FIG. 5 is a structural diagram illustrating a further modification of the waste treatment system of FIG. 1.

Another conceivable modification of the system of FIG. 1 is a system as shown in FIG. 5 where a fuel cell 900 is connected to electrolytic bath 700. Fuel cell 900 uses, as fuel, hydrogen gas generated in electrolytic bath 700 in accordance with equation (1) above. Compost 400 and bubble separating bath 800 shown in FIG. 1 are again not shown in FIG. 5.

In the system of FIG. 5, the hydrogen gas generated in electrolytic bath 700 is provided to fuel cell 900 by a well-known technique. In fuel cell 900, electric power and water are generated as the hydrogen provided is converted to water. The electric power thus generated is fed to the electrodes in electrolytic bath 700 as appropriate. Fuel cell 900 is equipped with a stabilizer device for stabilizing voltage and/or current of the electric power being fed to a constant value. The electric power is fed from fuel cell 900 to the electrodes in electrolytic bath 700 via the stabilizer device.

In the case where electric conductivity of the liquid in electrolytic bath 700 becomes higher than required, it is preferable that the water generated in fuel cell 900 is supplied into electrolytic bath 700 to lower the conductivity.

If the system is provided with a tank for storing an electrolysis accelerating agent to supply to electrolytic bath 700, the water generated in fuel cell 900 may be provided to the tank for use as a solvent.

Figure 6:
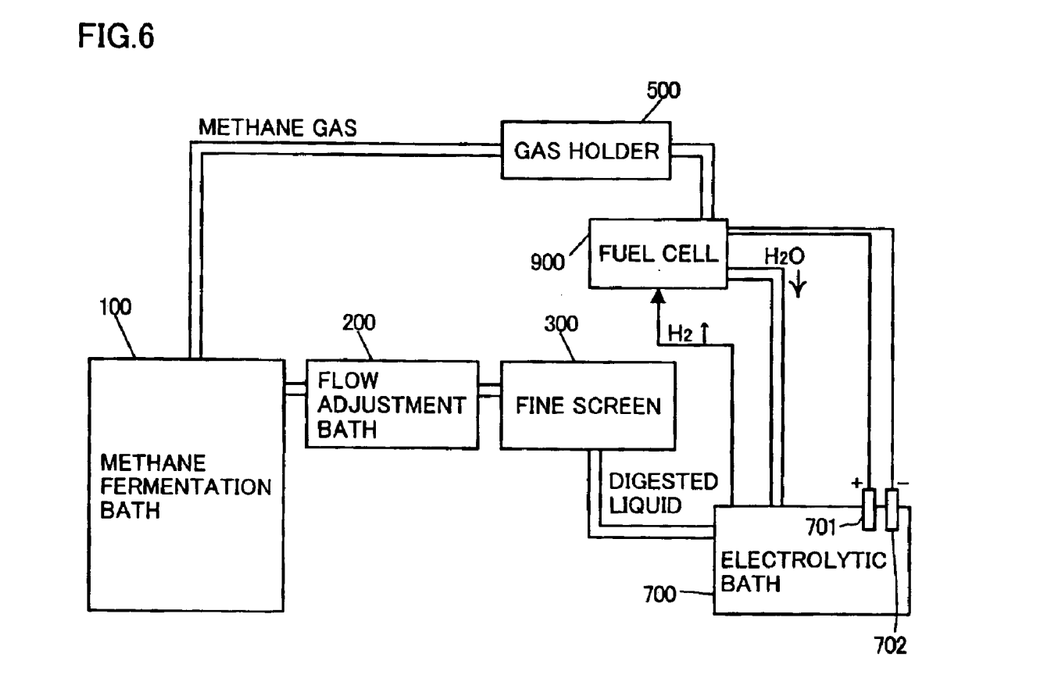
FIG. 6 is a structural diagram illustrating a still further modification of the waste treatment system of FIG. 1.

A still further modification of the system of FIG. 1 is shown in FIG. 6. In the system shown in FIG. 5, the methane gas introduced into gas holder 500 has been provided to electric generator 600 for use as fuel. By comparison, in the system shown in FIG. 6, the methane gas introduced into gas holder 500 is provided to fuel cell 900 to be used as fuel for generation of electric power in fuel cell 900. That is, the system shown in FIG. 6 includes fuel cell 900, instead of electric generator 600, as the electric generating device of the present invention. As such, in the system of FIG. 6, fuel cell 900 feeds electric power to electrodes 701, 702, instead of electric generator 600 in the case of the system of FIG. 4.

Thus, in the system shown in FIG. 6, electric generator 600 becomes unnecessary, compared to the system shown in FIG. 5. This can reduce the cost for construction of the system. In addition, in the system of FIG. 6, the DC power generated in fuel cell 900 can directly be fed to electrodes 701, 702. Thus, the conversion of the AC power to the DC power in electric generator 600 having been necessary in the systems of FIGS. 4 and 5 becomes unnecessary. This is advantageous, not only in that a device for the conversion is no longer required, but also in that power loss during the conversion can be suppressed.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A waste treatment system, comprising:
   an electric generating device generating electric power using a valuable substance recovered from organic waste as fuel;
   a methane fermentation bath anaerobically fermenting said organic waste; and
   an electrolytic bath into which digested liquid generated upon fermentation in said methane fermentation bath is introduced,
   said electrolytic bath having an electrode pair fed with the electric power from said electric generating device.

2. The waste treatment system according to claim 1, further comprising a bubble separating portion separating bubbles from the liquid in said electrolytic bath.

3. The waste treatment system according to claim 1, wherein said electrode pair includes an anode electrode formed of platinum or a conductor containing platinum, and a cathode electrode formed of a copper-zinc alloy, a conductor containing iron, or a conductor containing aluminum.

4. The waste treatment system according to claim 1, further comprising a surfactant adding portion adding a surfactant to the digested liquid introduced into said electrolytic bath.

5. The waste treatment system according to claim 1, further comprising a chemical agent adding portion adding chloride or hypochlorite to the digested liquid introduced into said electrolytic bath.

6. The waste treatment system according to claim 1, further comprising a polarity control portion inverting polarities of potentials applied from said electric generating device to said electrode pair.

7. The waste treatment system according to claim 1, further comprising a solid matter separating portion separating a solid matter from the digested liquid before the digested liquid is introduced into said electrolytic bath.

8. The waste treatment system according to claim 7, wherein said solid matter separating portion is formed of a film separating the solid matter having a particle size equal to or greater than a prescribed size from the digested liquid.

9. The waste treatment system according to claim 1, wherein said electric generating device outputs direct current power.

10. The waste treatment system according to claim 9, wherein said electric generating device outputs direct current power of a constant current or a constant voltage.

11. The waste treatment system according to claim 1, wherein said electric generating device and said electrolytic bath are configured integrally.

* * * * *